United States Patent
Lee et al.

(10) Patent No.: US 8,338,167 B2
(45) Date of Patent: Dec. 25, 2012

(54) PRESSURE CONTROLLABLE INCUBATION SYSTEM

(75) Inventors: Eunil Lee, Seoul (KR); Sangnam Oh, Seoul (KR)

(73) Assignee: Korea University Industrial & Academic Collaboration Foundation, Seoul (KR)

( * ) Notice: Subject to any disclaimer, the term of this patent is extended or adjusted under 35 U.S.C. 154(b) by 931 days.

(21) Appl. No.: 11/942,137

(22) Filed: Nov. 19, 2007

(65) Prior Publication Data

US 2008/0199944 A1    Aug. 21, 2008

(30) Foreign Application Priority Data

Feb. 16, 2007   (KR) .................. 10-2007-0016834

(51) Int. Cl.
| | |
|---|---|
| *C12M 1/00* | (2006.01) |
| *C12M 3/00* | (2006.01) |
| *C12M 1/34* | (2006.01) |
| *C12M 1/36* | (2006.01) |
| *C12M 1/38* | (2006.01) |
| *G02B 21/26* | (2006.01) |
| *G02B 21/34* | (2006.01) |
| *G01N 21/01* | (2006.01) |

(52) U.S. Cl. .............. 435/303.1; 435/286.5; 435/288.7; 359/395; 359/398

(58) Field of Classification Search .... 435/303.1–303.3, 435/286.5, 288.7; 359/395, 398
See application file for complete search history.

(56) References Cited

U.S. PATENT DOCUMENTS

| | | | | |
|---|---|---|---|---|
| 4,188,265 | A | * | 2/1980 | Larro ......................... 435/303.2 |
| 4,892,830 | A | * | 1/1990 | Findley et al. ............. 435/286.6 |
| 6,518,059 | B1 | * | 2/2003 | Butts .......................... 435/303.1 |
| 2005/0032199 | A1 | * | 2/2005 | Takahashi .................. 435/286.5 |
| 2005/0084420 | A1 | * | 4/2005 | Osawa et al. .............. 435/303.1 |
| 2006/0057713 | A1 | * | 3/2006 | Cecchi ....................... 435/303.1 |

FOREIGN PATENT DOCUMENTS

| | | |
|---|---|---|
| KR | 890004805 B1 | 11/1989 |
| KR | 20030061062 A | 7/2003 |

OTHER PUBLICATIONS

English Translation of Abstract; Korean Publication No. KR890004805(B1); Applicant: Shimadzu Corp; Published Nov. 27, 1989 (Abstract Only) (1 pg).

English Translation of Abstract; Korean Publication No. KR20030061062; Applicant: Sul, Dong Geun; Published Jul. 18, 2003 (Abstract Only) (2 pgs).

\* cited by examiner

*Primary Examiner* — Nathan Bowers
*Assistant Examiner* — Lydia Edwards
(74) *Attorney, Agent, or Firm* — Casimir Jones SC (57) ABSTRACT

A pressure controllable incubation system is provided for constantly maintaining a concentration of carbon dioxide while keeping a pressure chamber, in which living organisms to be cultured are placed, at a pressure higher than atmospheric pressure. The pressure controllable incubation system comprise a cylinder that stores air containing high-concentration carbon dioxide to be injected into a pressure chamber and supplies the air into the pressure chamber, and a heat controller that constantly maintains temperature in the pressure chamber. The pressure controllable incubation system constantly maintains culture conditions such as pressure, temperature, and concentration of carbon dioxide which the user wants for a long time, so that it can be effectively applied to the culture of various living organisms.

5 Claims, 5 Drawing Sheets

PRESSURE CONTROLLABLE INCUBATION SYSTEM

BACKGROUND OF THE INVENTION

1. Field of the Invention

The present invention relates generally to a pressure controllable incubation system. More particularly, the present invention relates to a pressure controllable incubation system capable of constantly maintaining a concentration of carbon dioxide while keeping a pressure chamber, in which living organisms to be cultured are placed, at a pressure higher than atmospheric pressure.

2. Description of the Prior Art

Such an incubation system is applied to a research on the diseases of the circulatory system relating to endothelial and muscular cells of blood vessels, glomerular cells, etc. of various animals cultured under pressure (about 1.2 ata) corresponding to high blood pressure of a human being, a research on the dentistry relating to alveolar bone and periodontal ligament cells, a research on the influence which mechanical and physical stimuli such as pressure exert on chondrogenic differentiation of cartilaginous cells and stem cells, and so on. Furthermore, the incubation system is also applied to a research on hyperbaric oxygen therapy that has been used to cure injuries, hypoxia, decompression sickness, diver's disease, carbon monoxide poisoning, etc. for a long time by pressurizing 100% oxygen outside the organism at 2 through 4 ata for a short time, and a research on oxidative stress and antioxidants of cells or individuals.

In order to study biological influences which the "pressure" exerts on the cells or organisms such as nematodes indispensable to make this research, various conditions such as pressure, temperature, concentration of carbon dioxide, etc. must be invariably maintained. To this end, an apparatus or system for applying the pressure to the cells or organisms such as nematodes has been provided.

This related apparatus or system includes a technique of injecting 95% air and 5% carbon dioxide into a big bottle using a 25-gauge needle (Watanabe et al., Saga University in Japan, 1987), a technique of directly inserting a pressure chamber into a carbon dioxide incubator and adjusting a concentration of carbon dioxide to 5% (Kato et al., Kurume University in Japan, 1994), and so on. Further, a technique of installing a variety of lead ingots on a piston and adjusting pressure (Yamamoto et al., Osaka University in Japan, 1991) was proposed. Recently, a technique of measuring and adjusting pressure in an incubator using a solid-state sensor and a compressor at the same time (Chris Healey et al., The University of Vermont in USA, 2003) has been proposed.

Most of these related incubation systems employ the technique of applying pressure to a chamber using an air or oil pump system and a solenoid valve, and are not suitable to meet experimental conditions for culturing the cells or organisms such as nematodes, i.e. conditions for maintaining the carbon dioxide concentration of 5% for a long time. For this reason, the related pressure controllable incubation systems for culturing living organisms have difficulty in obtaining reliable accurate results.

Further, these incubation systems are structurally complicated to increase a volume of constituents installed therein, and require careful management due to troublesome operation and frequent malfunction. Furthermore, these incubation systems are not suitable for an experiment of applying the pressure to the nematodes, which are small experimental animals having a very high value of the biological research. Thus, the influences which the pressure exerts on the organisms are merely observed within the limits of the animal cells. Consequently, the researches on the influences which the pressure exerts on the individuals make difficult progress.

SUMMARY OF THE INVENTION

Accordingly, the present invention has been made keeping in mind the above problems occurring in the prior art, and an object of the present invention is to provide a pressure controllable incubation system, which stably maintains specific values of pressure, temperature, and concentration of carbon dioxide that are basic conditions for culturing living organisms for a long time, and provides easy operation and small volume through a compact structure.

Another object of the present invention is to provide a pressure controllable incubation system, which enables conversion into necessary culture conditions according to each target to be cultured.

To accomplish the above objects, according to one aspect of the present invention, there is provided a pressure controllable incubation system for culturing living organisms. The pressure controllable incubation system comprises: a pressure chamber that placing the living organisms to be cultured; a cylinder that is coupled with the pressure chamber, and stores air containing high-concentration carbon dioxide to be injected into the pressure chamber; a vacuum pump that is coupled with the pressure chamber, and discharges the air in the pressure chamber; a heat controller that detects temperature in the pressure chamber through a temperature sensor, and supplies heat to the pressure chamber based on the detected temperature; a pressure converter that detects pressure in the pressure chamber through a pressure sensor, and converts the detected pressure into a numerical value; and a monitor that displays the converted pressure value.

The pressure controllable incubation system may further comprise: a pressure applying valve that is installed on a hose connecting the cylinder and the pressure chamber, and adjusts an amount of the air containing high-concentration carbon dioxide introduced into the pressure chamber; and a pressure releasing valve that is installed on a hose connecting the vacuum pump and the pressure chamber, and adjusts an amount of the air containing high-concentration carbon dioxide discharged from the pressure chamber to the vacuum pump.

The pressure controllable incubation system may further comprise an air heater that heats the air containing high-concentration carbon dioxide introduced from the cylinder into the pressure chamber at a predetermined temperature before the air containing high-concentration carbon dioxide is introduced into the pressure chamber.

Further, the air containing high-concentration carbon dioxide may contain the carbon dioxide at the rate from 5% to 10%.

Meanwhile, the pressure chamber may comprise: a heat insulating jacket that is enclosed around the pressure chamber; a plurality of bearing legs that support the pressure chamber on a ground surface, and adjust a height of the pressure chamber with respect to the ground surface; and an openable door 5 that includes a pressure window 19 so as to be able to observe the living organisms placed in the pressure chamber.

Further, the pressure chamber may include a cylindrical chamber that has an inner diameter of 300 mm and a length of 600 mm.

Meanwhile, the heat controller may comprise a heat supply that supplies electrical energy to the pressure chamber when the temperature in the pressure chamber is lowered and increases the temperature in the pressure chamber.

The heat controller may further comprise at least one current-voltage monitor that displays values of current and voltage supplied to the pressure chamber through the heat supply.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

Hereinafter, a pressure controllable incubation system according to an embodiment of the present invention will be described in detail with reference to the accompanying drawings.

Figure 1:
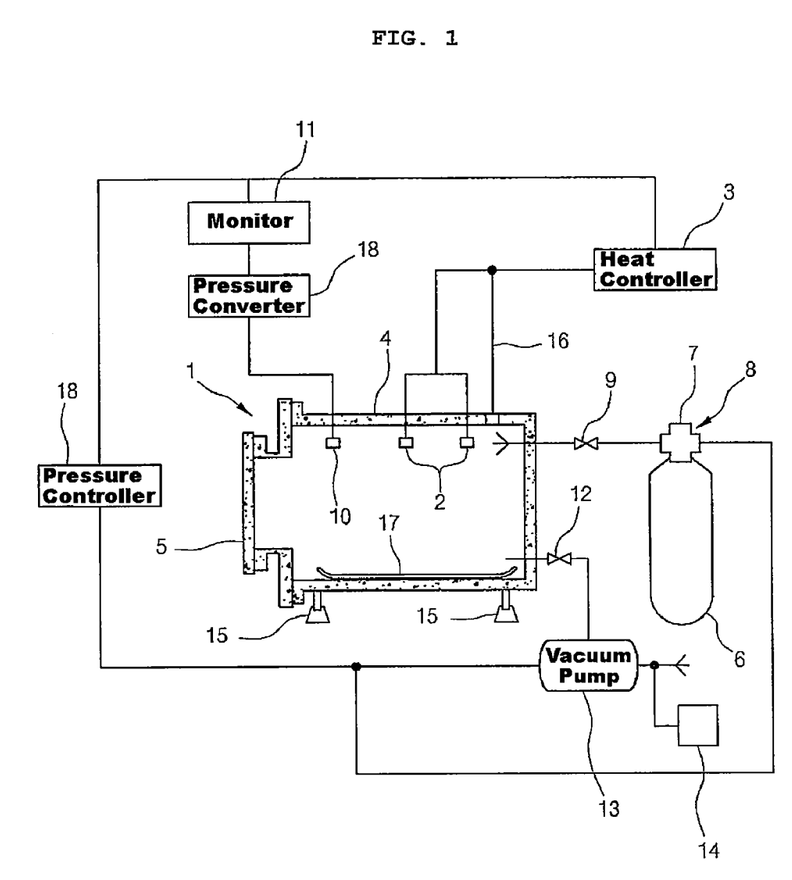
FIG. 1 is a layout view illustrating a pressure controllable incubation system according to an embodiment of the present invention.

Referring to FIG. 1, the pressure controllable incubation system according to an embodiment of the present invention comprises a pressure chamber 1 in which living organisms to be cultured are placed, a cylinder 6 that stores air containing high-concentration carbon dioxide injected into the pressure chamber 1 and is connected with the pressure chamber 1, a vacuum pump 13 that is connected with the pressure chamber 1 and discharges the air in the pressure chamber 1, a heat controller 3 that detects an internal temperature of the pressure chamber 1 through at least one temperature sensor 2 and applies heat to the pressure chamber 1, a pressure converter 18 that converts the internal pressure of the pressure chamber 1 which is measured by a pressure sensor 10 into a numerical value, and a monitor 11 that displays the converted pressure value. Further, the pressure controllable incubation system includes a carbon dioxide sensor 14 that detects a concentration of carbon dioxide in the air pumped by the vacuum pump 13.

Figure 2:
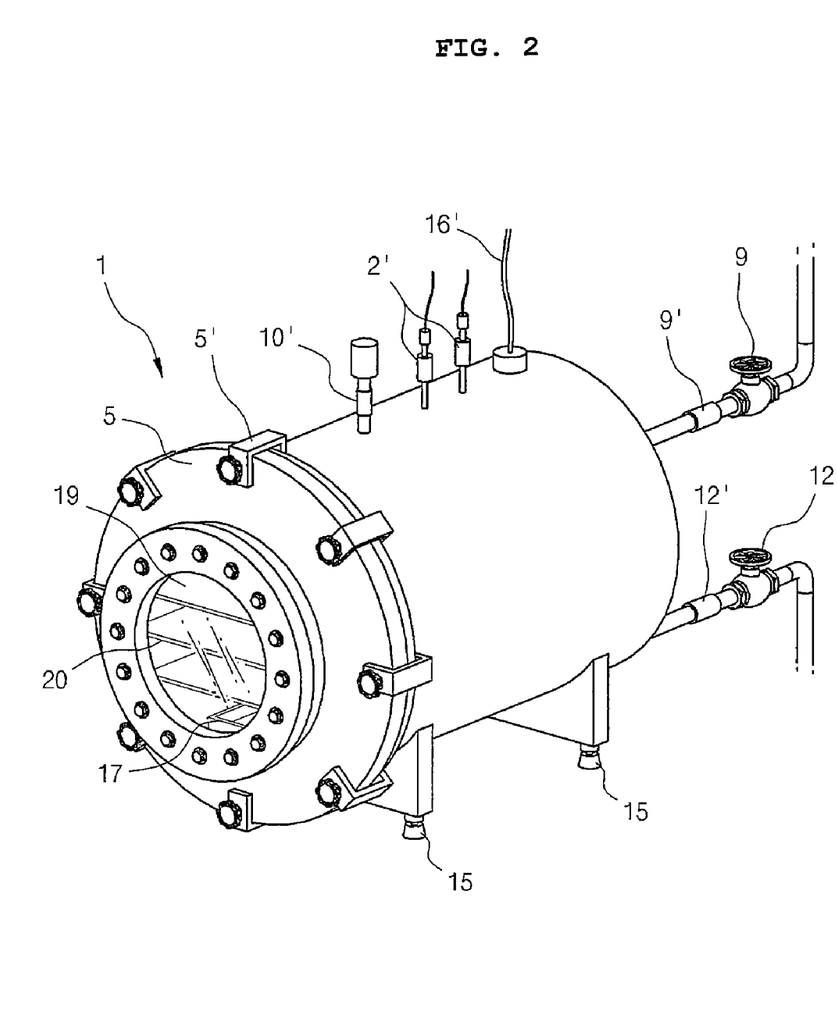
FIG. 2 is a perspective view illustrating a pressure chamber of the pressure controllable incubation system of FIG. 1.

The pressure chamber 1 includes at least one tray 20 that contains the living organisms to be cultured, and a drain tray 17 that adjusts moisture in the pressure chamber 1 (see FIG. 2).

Further, both the temperature sensor 2 for measuring the temperature in the pressure chamber 1 and the pressure sensor 10 are installed in the pressure chamber 1. And they are each connected with the heat controller 3 and the pressure converter 18 through a temperature sensor coupler 2' and a pressure sensor coupler 10' which communicate with the outside of the pressure chamber 1 respectively (see FIG. 2), so that they provide information on the temperature and pressure in the pressure chamber 1.

Herein, the temperature sensor coupler 2' and the pressure sensor coupler 10' are collectively defined as "couplers." Further, these "couplers" include a pressure applying coupler 9' and a pressure releasing coupler 12', to which hoses for connecting the cylinder 6 and the vacuum pump 13 to the pressure chamber 1 are coupled. These "couplers" are preferably produced under the same standards such that they can be changed in position according to circumstances.

Each "hose" refers to a pipe having an internal space in order to deliver an ordinary liquid or fluid. Although the connection between the respective constituents is plotted as a straight line in FIG. 1, the hoses are naturally used for portions where gas flows in the pressure controllable incubation system according to an embodiment of the present invention, and so the description thereof will be omitted.

A heat insulating jacket 4 is enclosed around the pressure chamber 1 in order to constantly maintain the internal temperature of the pressure chamber 1. Preferably, the heat insulating jacket 4 is made of silicon, and is hermetically sealed around the pressure chamber 1. However, in either case, as long as the internal temperature of the pressure chamber 1 can be prevented from being lowered due to a temperature difference between the pressure chamber 1 and the external air, any material can be used.

Referring to FIGS. 1 and 2, the pressure chamber 1 is preferably provided with an openable door 5 that includes a pressure window 19 so as to be able to observe the living organisms placed in the pressure chamber from the outside, and a plurality of bearing legs 15 that support the pressure chamber 1 on the ground surface and adjust a height of the pressure chamber 1 with respect to the ground surface.

The pressure window 19 is made of material, such as glass, having rigidity capable of sufficiently withstanding the atmospheric pressure or more. Of course, the material can be replaced with plastic. In either case, it will do if the material has transparency so as to be able to observe the inside of the pressure chamber and enough rigidity to withstand the atmospheric pressure or more, e.g. the pressure from 1 ata to 5 ata.

The door 5 is installed on one side of the pressure chamber 1, and is formed so as to be opened and closed using a hinge (not shown). Alternatively, the door 5 may be formed so as to be separated from the pressure chamber 1 without a hinge. In either case, the door 5 must be able to hermetically close the pressure chamber 1. Thus, as illustrated in FIG. 2, a plurality of fasteners 5' are preferably installed along the outer circumference of the circular door at regular intervals. The fasteners 5' can be firmly fastened using screwed bolts. Further, an elastic member (not shown) is preferably interposed between the door and the pressure chamber, and thereby the door 5 is sealed so as to prevent the air in the pressure chamber 1 from leaking out when closed.

The bearing legs 15 adjust the pressure chamber 1 with respect to the ground surface such that the pressure chamber 1 is horizontal to the ground surface. Thus, when the ground surface is uneven, the pressure chamber 1 can be horizontally maintained by adjusting the height of each bearing leg 15. As illustrated in FIG. 2, the number of bearing legs 15 is preferably set properly. Each bearing leg 15 is preferably screwed to the pressure chamber 1, so that the height thereof can be adjusted by rotation. Of course, the height of each bearing leg 15 may be adjusted using a proper physical structure other than the screwed structure. In either case, the height of each bearing leg 15 must be able to be adjusted freely.

The pressure chamber 1 is not specially limited in size. However, the pressure chamber 1 included in the pressure controllable incubation system according to an embodiment of the present invention preferably has an inner diameter of 300 mm and a length of 600 mm. Further, the pressure chamber 1 has a weight of 50 kg, and thus is very lightweight compared to that of an existing incubation system. However, as a result of testing, the pressure chamber 1 could sufficiently accommodate a total of 50 culture plates having a diameter of 100 mm. In addition, the pressure chamber can be very easily moved due to the shape of a small cylinder, meet desired experimental conditions within a short time due to a volume reduced to a maximum extent, and prevent excessive consumption of energy due to reduction of an unnecessary space.

Figure 3:
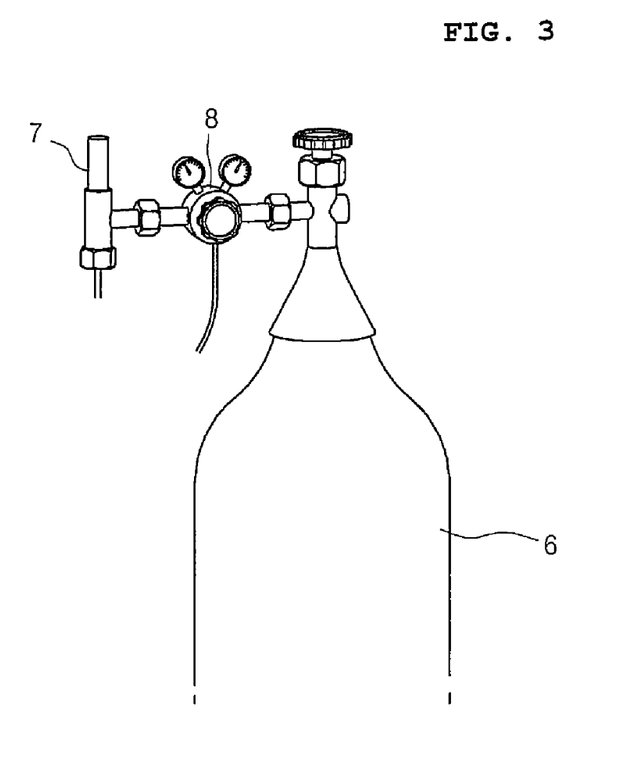
FIG. 3 is a perspective view illustrating a cylinder of the pressure controllable incubation system of FIG. 1.

Referring to FIGS. 1 and 3, the pressure controllable incubation system according to an embodiment of the present invention includes the cylinder 6, an air heater 8 coupled to the cylinder 6, and a pressure controller 7 coupled to the air heater 8.

The cylinder 6 refers to an ordinary container used to store and transport compressed gas. The cylinder 6 is stored therein with air containing high-concentration carbon dioxide.

In the related art, in order to constantly maintain a concentration of carbon dioxide as the culture conditions, ordinary air and carbon dioxide gas are separately stored, are injected into an incubator, and are mixed in the incubator. In contrast, in the present invention, air containing high-concentration carbon dioxide, which is calculated and prepared at a desired concentration, is previously stored in the cylinder 6, and then is injected into the pressure chamber 1 through a hose (not shown) coupled to the pressure chamber 1, so that the carbon dioxide concentration and the air pressure can be adjusted in the pressure chamber 1 at the same time. This is based on the principle of static dilution used in preparing standard gas.

Referring to Table 1 below, in the event that the air containing carbon dioxide at a concentration of 5% or 10% is injected, the carbon dioxide concentration in the pressure chamber 1 according to various values of pressure is represented. This is ultimately to make the carbon dioxide concentration of 5%, which is a theoretical experimental value that can be adjusted within the range of 5±0.15%. The carbon dioxide concentration in the pressure chamber 1 can be made as shown in Table 1 by repeating injection and discharge of the air containing high-concentration carbon dioxide for a short time (about 3 minutes). In Table 1, the parts making the atmosphere absolute (ata) value with an asterisk (*) are subjected to discharge of the air containing high-concentration carbon dioxide in order to adjust the pressure after the air containing high-concentration carbon dioxide is injected. Because external air can't be inflowed, so they have low experimental error in the carbon dioxide concentration and maintain pH within a stable range.

TABLE 1

| Atmosphere Absolute (ata) | 1 (in chamber) | 1.2* | 1.2* | 1.2* | 1.2 | Injected Gas |
|---|---|---|---|---|---|---|
| Bar (displayed pressure) | 0 | 0.203 | 0.203 | 0.203 | 0.203 | 10% $CO_2$ + 90% air ($O_2$ 18.9% + $N_2$ 70.2%) |
| $CO_2$ (%) | 0.030 | 1.692 | 3.076 | 4.230 | 5.192 | pH |
| $O_2$ (%) | 21.000 | 20.650 | 20.358 | 20.115 | 19.913 | range: |
| $N_2$ (%) | 78.000 | 76.700 | 75.617 | 74.714 | 73.962 | 7.4 ± 0.2) |
| Balance (%) | 0.970 | 0.958 | 0.949 | 0.941 | 0.934 | |
| Total | 100.000 | 100.000 | 100.000 | 100.000 | 100.000 | |

| Atmosphere Absolute (ata) | 1 (in chamber) | 1.4* | 1.4 |
|---|---|---|---|
| Bar (displayed pressure) | 0 | 0.405 | 0.405 |
| $CO_2$ (%) | 0.030 | 2.879 | 4.913 |
| $O_2$ (%) | 21.000 | 20.400 | 19.971 |
| $N_2$ (%) | 78.000 | 75.771 | 74.180 |
| Balance (%) | 0.970 | 0.950 | 0.936 |
| Total | 100.000 | 100.000 | 100.000 |

| Atmosphere Absolute (ata) | 1 (in chamber) | 1.6* | 1.4* | 1.6 |
|---|---|---|---|---|
| Bar (displayed pressure) | 0 | 0.608 | 0.405 | 0.608 |
| $CO_2$ (%) | 0.030 | 3.769 | 3.769 | 4.807 |
| $O_2$ (%) | 21.000 | 20.213 | 20.213 | 19.994 |
| $N_2$ (%) | 78.000 | 75.075 | 75.075 | 74.263 |
| Balance (%) | 0.970 | 0.944 | 0.944 | 0.936 |
| Total | 100.000 | 100.000 | 100.000 | 100.000 |

| Atmosphere Absolute (ata) | 1 (in chamber) | 1.8* | 1.7* | 1.8 |
|---|---|---|---|---|
| Bar (displayed pressure) | 0 | 0.811 | 0.709 | 0.811 |
| $CO_2$ (%) | 0.030 | 4.461 | 4.461 | 4.965 |
| $O_2$ (%) | 21.000 | 20.067 | 20.067 | 19.961 |
| $N_2$ (%) | 78.000 | 47.533 | 74.533 | 74.139 |
| Balance (%) | 0.970 | 0.939 | 0.939 | 0.935 |
| Total | 100.000 | 100.000 | 100.000 | 100.000 |

TABLE 1-continued

| Atmosphere Absolute (ata) | 1 (in chamber) | 2.0 | | | | |
|---|---|---|---|---|---|---|
| Bar (displayed pressure) | 0 | 1.013 | | | | |
| CO$_2$ (%) | 0.030 | 5.015 | | | | |
| O$_2$ (%) | 21.000 | 19.950 | | | | |
| N$_2$ (%) | 78.000 | 74.100 | | | | |
| Balance (%) | 0.970 | 0.935 | | | | |
| Total | 100.000 | 100.000 | | | | |
| Atmosphere Absolute (ata) | 1 (in chamber) | 2.2* | 2.2* | 2.2* | 2.2 | Injected Gas |
| Bar (displayed pressure) | 0 | 1.216 | 1.216 | 1.216 | 1.216 | 5% CO$_2$ + 95% air (O$_2$ 19.9% + N$_2$ 74.1%) pH range: 7.3 ± 0.2) |
| CO$_2$ (%) | 0.030 | 2.741 | 3.973 | 4.533 | 4.788 | |
| O$_2$ (%) | 21.000 | 20.427 | 20.167 | 20.049 | 19.995 | |
| N$_2$ (%) | 78.000 | 75.873 | 74.906 | 74.466 | 74.266 | |
| Balance (%) | 0.970 | 0.959 | 0.954 | 0.952 | 0.951 | |
| Total | 100.000 | 100.000 | 100.000 | 100.000 | 100.000 | |
| Atmosphere Absolute (ata) | 1 (in chamber) | 2.4* | 2.4* | 2.4* | 2.4 | |
| Bar (displayed pressure) | 0 | 1.419 | 1.419 | 1.419 | 1.419 | |
| CO$_2$ (%) | 0.030 | 2.929 | 4.137 | 4.640 | 4.850 | |
| O$_2$ (%) | 21.000 | 20.388 | 20.132 | 20.026 | 19.982 | |
| N$_2$ (%) | 78.000 | 75.725 | 74.777 | 74.382 | 74.218 | |
| Balance (%) | 0.970 | 0.958 | 0.953 | 0.951 | 0.951 | |
| Total | 100.000 | 100.000 | 100.000 | 100.000 | 100.000 | |
| Atmosphere Absolute (ata) | 1 (in chamber) | 2.6* | 2.6* | 2.6* | 2.6 | |
| Bar (displayed pressure) | 0 | 1.621 | 1.621 | 1.621 | 1.621 | |
| CO$_2$ (%) | 0.030 | 3.088 | 4.265 | 4.717 | 4.891 | |
| O$_2$ (%) | 21.000 | 20.354 | 20.105 | 20.010 | 19.973 | |
| N$_2$ (%) | 78.000 | 75.600 | 74.677 | 74.322 | 74.185 | |
| Balance (%) | 0.970 | 0.958 | 0.953 | 0.951 | 0.950 | |
| Total | 100.000 | 100.000 | 100.000 | 100.000 | 100.000 | |
| Atmosphere Absolute (ata) | 1 (in chamber) | 2.8* | 2.8* | 2.8* | 2.8 | |
| Bar (displayed pressure) | 0 | 1.824 | 1.824 | 1.824 | 1.824 | |
| CO$_2$ (%) | 0.030 | 3.255 | 4.366 | 4.774 | 4.919 | |
| O$_2$ (%) | 21.000 | 20.325 | 20.084 | 19.998 | 19.967 | |
| N$_2$ (%) | 78.000 | 75.493 | 74.597 | 74.278 | 74.163 | |
| Balance (%) | 0.970 | 0.957 | 0.953 | 0.951 | 0.950 | |
| Total | 100.000 | 100.000 | 100.000 | 100.000 | 100.000 | |
| Atmosphere Absolute (ata) | 1 (in chamber) | 3* | 3* | 3* | 3 | |
| Bar (displayed pressure) | 0 | 2.027 | 2.027 | 2.027 | 2.027 | |
| CO$_2$ (%) | 0.030 | 3.343 | 4.448 | 4.816 | 4.939 | |
| O$_2$ (%) | 21.000 | 20.300 | 20.067 | 19.989 | 19.963 | |
| N$_2$ (%) | 78.000 | 75.400 | 74.533 | 74.244 | 74.148 | |
| Balance (%) | 0.970 | 0.957 | 0.952 | 0.951 | 0.950 | |
| Total | 100.000 | 100.000 | 100.000 | 100.000 | 100.000 | |

Referring to FIGS. 1 and 2, the air containing high-concentration carbon dioxide is injected from the cylinder 6 into the pressure chamber 1 through the hose (not shown) connecting the cylinder 6 and the pressure chamber 1.

A pressure applying valve 9 is installed on a hose (not shown) coupled to the pressure applying coupler 9', so that it can adjust an amount of the air containing high-concentration carbon dioxide introduced into the pressure chamber 1.

A pressure releasing valve 12 is installed on a hose (not shown) coupled to the pressure releasing coupler 12', so that it can adjust an amount of the air in the pressure chamber 1 released to the vacuum pump 13.

The pressure in the pressure chamber 1 is measured by the pressure sensor 10, is converted into a numerical value by the pressure converter 18, and is displayed on the monitor 11. Here, the pressure converter 18 can be interpreted as including the pressure sensor 10.

Figure 4:
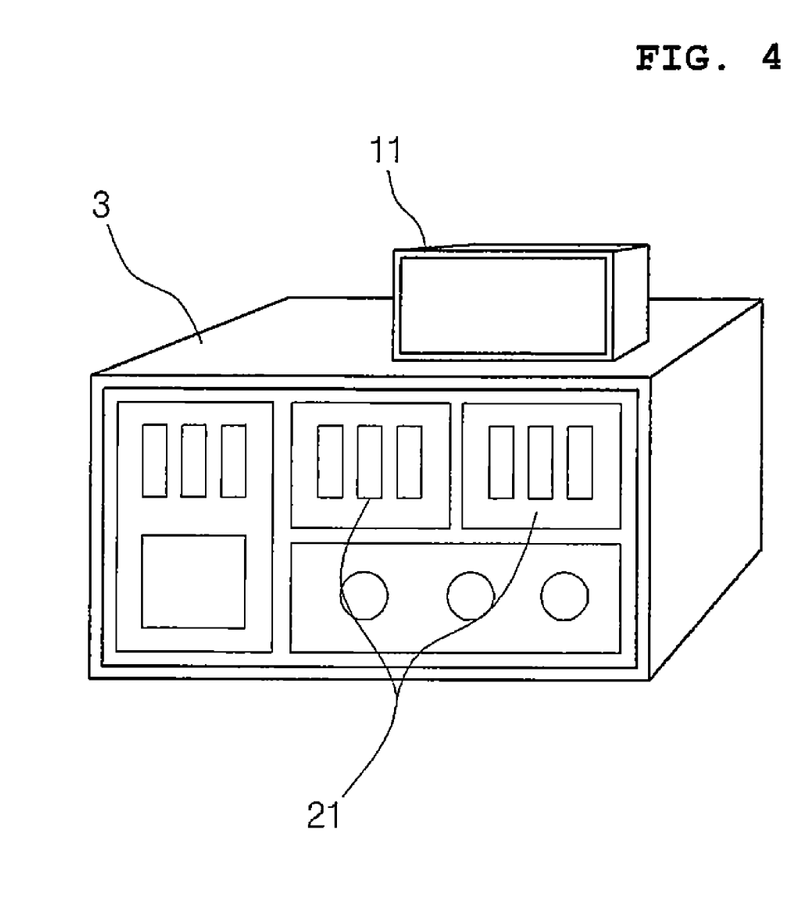
FIG. 4 is a perspective view illustrating a heat controller and a monitor of the pressure controllable incubation system of FIG. 1.

The monitor 11 refers to a device that converts the numerical value converted by the pressure converter 18 into an electrical signal and then displays the electrical signal into a symbol such as a figure which the user can recognize. As illustrated in FIG. 4, the monitor 11 can be independent of the heat controller 3, or be integrated with the heat controller 3. Alternatively, the monitor 11 may also perform the function of a current-voltage monitor.

The user looks at the pressure value displayed on the monitor 11 to adjust the pressure applying valve 9 and the pressure releasing valve 12, so that he/she can set the pressure in the pressure chamber 1 to a proper value. Of course, in the event that the pressure applying valve 9, the pressure releasing valve 12, the pressure converter 18, the pressure sensor 10, and the monitor 11 are connected to a controller (not shown) having electronic circuitry, this can be established into an automatic control system in which, when a pressure value (target value) to be set is input, the target value can be automatically adjusted to a change in pressure.

Referring to FIG. 3 again, the air containing high-concentration carbon dioxide supplied from the cylinder 6 passes through the air heater 8 prior to the injection into the pressure chamber 1 such that it can be pre-heated to meet an optimal temperature condition (e.g. 37° C.) of the living organisms that will be placed and cultured in the pressure chamber 1. The air heater 8 is powered to maintain a stable temperature in connection with the heat controller 3. Of course, the electrical energy may be replaced by another type of energy such as chemical energy. Preferably, in order to accurately adjust a proper temperature which the user wants, an electronic circuitry based control system capable of uniformly controlling current and voltage of supplied electrical energy is used.

The pressure controller 7 functions to introduce the supplied air containing high-concentration carbon dioxide into the pressure chamber 1 while constantly maintaining the pressure of the supplied air. This pressure controller 7 can make use of an existing pressure regulator, or the like.

Referring to FIG. 4, the heat controller 3 includes a heat supply 16 (see FIG. 1) that supplies electrical energy to the pressure chamber 1 when the temperature in the pressure chamber 1 is lowered and thus increases the temperature in the pressure chamber 1, and at least one current-voltage monitor 21 that displays values of current and voltage supplied to the pressure chamber through the heat supply.

The temperature sensor 2 is installed in the pressure chamber 1 through the temperature sensor coupler 2', detects the temperature in the pressure chamber 1, and transmits the detected temperature to the heat controller 3.

The heat controller 3 determines whether the temperature in the pressure chamber 1 is higher or lower than a fixed temperature (e.g. 37° C.) which the user wants on the basis of the information transmitted from the temperature sensor 2. In that case, the heat controller 3 blocks or increases the electrical energy supplied to the pressure chamber 1 through the heat supply 16, thereby constantly maintaining the temperature in the pressure chamber 1.

The heat supply 16 includes a heat supply line 16', which is connected between the heat controller 3 and the pressure chamber 1. The pressure chamber 1 can be provided with an electric resistor (not shown) so as to supply heat thereto. Thereby, the supplied electrical energy can be converted into thermal energy.

Because the heat controller 3 is equipped with the current-voltage monitor 21 capable of displaying the values of the current and voltage supplied through the heat supply line, the user can adjust the heat controller so as to supply proper current and voltage. Of course, in order to automatically maintain the target temperature that is preset in the pressure chamber 1 by the user, use may be made of a control system of allowing the heat controller 3 to receive the temperature detected by the temperature sensor 2 and to automatically control the electrical energy to be supplied to the pressure chamber 1 through the heat supply 16 when the received temperature is higher or lower than the target temperature.

In the embodiment of the present invention, the temperature in the pressure chamber 1 was 37.1±0.33° C. with respect to the temperature of 37° C. set by the user, and thus shown a slight change and a very stable state. Furthermore, after the air of 2 ata is injected into the pressure chamber 1, the pressure controllable incubation system according to the present invention is continuously operated for 2 to 3 weeks. Even in this case, the temperature and pressure in the pressure chamber 1 are constantly maintained.

Figure 5:
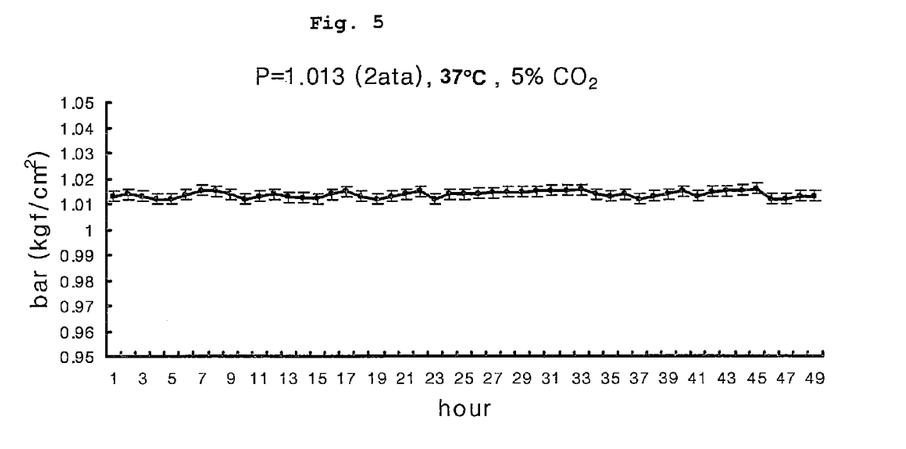
FIG. 5 is a graph illustrating pressure over time in a pressure chamber while the pressure controllable incubation system of FIG. 1 is operated.
Figure 6:
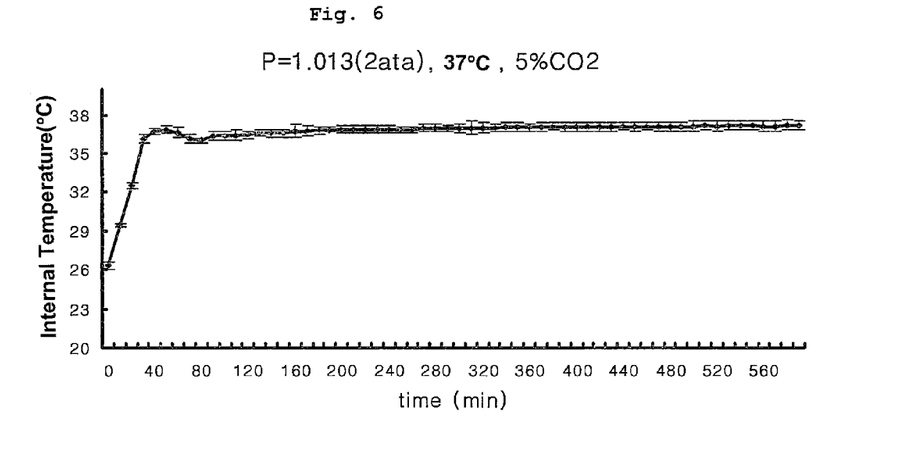
FIG. 6 is a graph illustrating temperature over time in a pressure chamber while the pressure controllable incubation system of FIG. 1 is operated.

Referring to FIGS. 5 and 6, it can be found that the temperature and pressure in the pressure chamber 1 are constantly maintained while the pressure controllable incubation system according to an embodiment of the present invention is operated. Especially, it can be found that the pressure chamber maintains 2 ata for a long time of 40 hours or more, reaches the target temperature of 37° C. within 30 minutes after operated, and maintains a uniform temperature for a long time.

The pressure controllable incubation system according to an embodiment of the present invention can be used to culture *caenorhabditis elegans* (nematode), which is simple in the structure of an individual and is treated as an important experimental animal because the equivalence to a human gene is highly estimated. This *caenorhabditis elegans* is cultured at a temperature of 25° C. without carbon dioxide. For this reason, in order to culture the *caenorhabditis elegans*, the temperature in the pressure chamber 1 is maintained at 25° C., and the cylinder 6 filled with the ordinary air rather than the air containing high-concentration carbon dioxide is coupled to the pressure chamber 1, and injects the air until the pressure chamber 1 reaches a desired pressure value. At this time, the air heater 8 is not operated. In this manner, the pressure controllable incubation system according to an embodiment of the present invention can easily make various experimental conditions according to various targets to be cultured.

As can be seen from the foregoing, the pressure controllable incubation system according to an embodiment of the present invention constantly maintains culture conditions such as pressure, temperature, concentration of carbon dioxide, etc. which the user wants for a long time, so that it can be effectively applied to the culture of various living organisms. Further, the inventive pressure controllable incubation system stores the air containing high-concentration carbon dioxide that is calculated and prepared at a desired concentration in one cylinder, and injects the stored air into the pressure chamber, so that it can adjust the concentration of carbon dioxide and the air pressure at the same time. Furthermore, the inventive pressure controllable incubation system makes use of the heat controller operated with electric energy, so that it can perform precise temperature adjustment. The inventive pressure controllable incubation system employs the pressure chamber having the shape of a small cylinder, so that it can be operated in a narrow place. In addition, with the inventive pressure controllable incubation system, the culture of the living organisms for the research influencing the human body can be effectively performed at the level of high blood pressure, so that the technical development of related research fields can be induced.

Although an exemplary embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A pressure controllable incubation system for culturing living organisms, comprising:
   a pressure chamber that placing the living organisms to be cultured;
   a cylinder that is coupled with the pressure chamber, and stores air containing carbon dioxide at a concentration from 5% to 10% to be injected into the pressure chamber;
   a vacuum pump that is coupled with the pressure chamber, and discharges the air in the pressure chamber;
   a heat controller that detects temperature in the pressure chamber through a temperature sensor, and supplies heat directly to the pressure chamber based on the detected temperature by supplying electrical energy to a heat supply connected between the heat controller and the pressure chamber when the temperature in the pressure chamber is lowered;
   a pressure converter that detects pressure in the pressure chamber through a pressure sensor, and converts the detected pressure into a numerical value; and
   a monitor that displays the converted pressure value wherein the air stored in the cylinder, containing high-concentration carbon dioxide at a concentration from 5% to 10%, is discharged from the cylinder at a predetermined pressure and supplied to the pressure chamber, wherein
   the pressure chamber is maintained at a pressure 1 atm higher than the predetermined pressure, such that the concentration of carbon dioxide at the pressure chamber is maintained at 5±0.15%.

2. The pressure controllable incubation system as claimed in claim 1, further comprising:
   a pressure applying valve that is installed on a hose connecting the bomb and the pressure chamber, and adjusts an amount of the air containing high-concentration carbon dioxide introduced into the pressure chamber; and
   a pressure releasing valve that is installed on a hose connecting the vacuum pump and the pressure chamber, and adjusts an amount of the air that is released from the pressure chamber to the vacuum pump.

3. The pressure controllable incubation system as claimed in claim 1, wherein the pressure chamber comprises:
   a heat insulating jacket that is enclosed around the pressure chamber in order to maintain the internal temperature of the pressure chamber;
   a plurality of bearing legs that support the pressure chamber on a ground surface, and adjust a height of the pressure chamber with respect to the ground surface; and
   an openable door that includes a pressure window so as to be able to observe the living organisms placed in the pressure chamber.

4. The pressure controllable incubation system as claimed in claim 3, wherein the pressure chamber includes a cylindrical chamber that has an inner diameter of below 300 mm and a length of below 600 mm.

5. The pressure controllable incubation system as claimed in claim 1, wherein the heat controller further comprises at least one current-voltage monitor that displays values of current and voltage supplied to the pressure chamber through the heat supply.

* * * * *